(12) United States Patent
Mori et al.

(10) Patent No.: US 7,998,723 B2
(45) Date of Patent: Aug. 16, 2011

(54) METHOD FOR FERMENTATIVE PRODUCTION OF N-ACETYL-D-GLUCOSAMINE BY MICROORGANISM

(75) Inventors: Tetsuya Mori, Atsugi (JP); Wakako Ichikawa, Atsugi (JP); Yuichi Kita, Atsugi (JP); Yasuyuki Tetsuka, Atsugi (JP)

(73) Assignee: Hokko Chemical Industry Co., Ltd., Chuo-ku, Tokyo (JP)

( * ) Notice: Subject to any disclaimer, the term of this patent is extended or adjusted under 35 U.S.C. 154(b) by 696 days.

(21) Appl. No.: 11/995,104

(22) PCT Filed: Jul. 14, 2006

(86) PCT No.: PCT/JP2006/314063
§ 371 (c)(1),
(2), (4) Date: Jan. 8, 2008

(87) PCT Pub. No.: WO2007/010855
PCT Pub. Date: Jan. 25, 2007

(65) Prior Publication Data
US 2010/0055746 A1      Mar. 4, 2010

(30) Foreign Application Priority Data
Jul. 19, 2005   (JP) ................. 2005-208160

(51) Int. Cl.
*C12N 1/14*     (2006.01)
(52) U.S. Cl. .................................................. 435/256.7
(58) Field of Classification Search ............... 435/252.3, 435/256.7
See application file for complete search history.

(56) References Cited

FOREIGN PATENT DOCUMENTS

| | | |
|---|---|---|
| JP | 63-273493 | 11/1988 |
| JP | 2000-281696 | 10/2000 |
| JP | 2000-513925 | 10/2000 |
| JP | 2001-078795 | 3/2001 |
| JP | 2004-041035 | 2/2004 |
| JP | 2004-283144 | 10/2004 |
| WO | WO 97/31121 | 8/1997 |
| WO | WO 2004/003175 | 1/2004 |

OTHER PUBLICATIONS

Andrade et al., Can. J. Chem. 70:2526-2535, 1992.*
Doi, Y., Mem. Natl. Sci. Mus. Tokyo, vol. 15, pp. 73-89, 1982.*
NBRC Catalogue, available on line at http://www.nbrc.nite.go.jp/NBRC2/NBRCDispSearchServlet?lang=en.; downloaded Sep. 12, 2010.*
Yoshikawa et al., Macromolecules 27:5471-5475, 1994.*
International Search Report dated Aug. 4, 2006.
Kajimoto, et al. "Therapeutic Effect of Milk Containing Natural-Type N-Acetyl-Glucosamine Against Knee Osteoarthritis," *New Medicines and Clinical J. New Rem. & Clin.*, vol. 52, No. 3, pp. 301-312, 2003.
Brown, et al. "Growth Kinetics and Cellulase Biosynthesis in the Continuous Culture of *Trichoderma viride*," *Biotechnology and Bioengineering*, vol. XIX, pp. 941-958, 1977.
Türker, et al. "Production of Cellulase by Freely Suspended and Immobilized Cells of *Trichoderma reesei*," *Enzyme Microb. Technol.* vol. 9, pp. 739-743, Dec. 1987.

* cited by examiner

*Primary Examiner* — Delia Ramirez
(74) *Attorney, Agent, or Firm* — Knobbe, Martens, Olson & Bear, LLP

(57) ABSTRACT

N-Acetyl-D-glucosamine can be produced by cultivating a fungus capable of producing N-acetyl-D-glucosamine, such as *Trichoderma hamatum* AB10282 strain (FERM BP-10623) or *Trichoderma harzianum* AB10283 strain (FERM BP-10624), in a culture medium supplemented with a carbon source other than chitin and chitin oligosaccharide and a nitrogen source to produce and accumulate N-acetyl-D-glucosamine in the culture medium and then collecting N-acetyl-D-glucosamine from the culture medium.

1 Claim, No Drawings

METHOD FOR FERMENTATIVE PRODUCTION OF N-ACETYL-D-GLUCOSAMINE BY MICROORGANISM

CROSS-REFERENCE TO RELATED APPLICATIONS

This application is the U.S. National Phase under 35 U.S.C. §371 of International Application PCT/JP2006/314063, filed Jul. 14, 2006, which was published in a non-English language, which claims priority to JP Application No. 2005-208160, filed Jul. 19, 2005.

TECHNICAL FIELD

The present invention relates to a novel microorganism having an ability to produce N-acetyl-D-glucosamine and a method of producing N-acetyl-D-glucosamine using the microorganism. N-acetyl-D-glucosamine is useful in the fields of drugs, health foods, foods, etc.

BACKGROUND ART

N-acetyl-D-glucosamine is a monosaccharide that makes up chitin contained in shells of crustacea such as crab and shrimp and is a nutrient contained in an extremely small amount in foods, and is also produced from chondrocytes in the body. N-acetyl-D-glucosamine is considered to have similar effects to that of glucosamine, and ingestion of N-acetyl-D-glucosamine is known to induce generation of novel cartilage and stop progression of osteoarthritis, or in some cases, to cure osteoarthritis (J. New Remedies and Clinics Vol. 52, No. 3, pp. 301-312, 2003). While glucosamine has a bitter taste, N-acetyl-D-glucosamine has a sweet taste 50% as sweet as sucrose and can be easily ingested, and therefore, N-acetyl-D-glucosamine has attracted attention as an alternative substance to glucosamine.

A conventional method of producing N-acetyl-D-glucosamine is performed by using shells of crustacea such as crab and shrimp as raw materials. Here is the outline of the method: N-acetyl-D-glucosamine is produced by steps of: crushing shells of crustacea; decalcifying the crushed products with a dilute acid; removing proteins with an alkali to yield purified chitin; hydrolyzing the resultant chitin with an acid to produce glucosamine; and then acetylating the resultant glucosamine with anhydrous acetic acid.

Meanwhile, conventional methods also include: a method involving partially hydrolyzing purified chitin with an acid (for example, see Patent Document 1); a method of producing N-acetyl-D-glucosamine by degrading chitin as a raw material with an enzyme produced by a microorganism_(for example, see Patent Document 2 and Patent Document 3); and a method involving partially hydrolyzing chitin with an acid and allowing an enzyme to react with the hydrolysate (for example, see Patent Document 4).

Conventional methods also include other production methods such as: a method of producing N-acetyl-D-glucosamine by culturing either chlorella cells infected with *Chlorovirus* or recombinant *Escherichia coli* introduced with a gene derived from *Chlorovirus* (for example, see Patent Document 5); and a method of producing N-acetyl-D-glucosamine by fermentation using a genetically modified microorganism, specifically, a genetically modified *Escherichia coli* (for example, see Patent Document 6).

Patent Document 1: JP 2000-281696 A
Patent Document 2: JP 2000-513925 A
Patent Document 3: JP 2004-41035 A
Patent Document 4: JP 63-273493 A
Patent Document 5: JP 2004-283144 A
Patent Document 6: WO 2004/003175

DISCLOSURE OF THE INVENTION

The above-mentioned methods of producing N-acetyl-D-glucosamine by chemically hydrolyzing shells of crustacea such as crab and shrimp as a material are performed by using high concentrations of acid solutions and alkaline solutions and therefore have a problem of producing large amounts of liquid wastes. Meanwhile, the method of producing N-acetyl-D-glucosamine by degrading chitin derived from shells of crustacea such as crab and shrimp with a microorganism or an enzyme produced by a microorganism has problems of low yield and high cost.

Meanwhile, if crustacea-allergic individuals ingest a product obtained by using shells of crab or shrimp as a raw material, allergic symptoms may be caused. Moreover, chitin as a material is obtained from fish resources, and its supply varies depending on fish catches. In recent years, there has been a fear that environmental disruption will be caused by overhunting.

In addition, the production method of N-acetyl-D-glucosamine by culturing chlorella cells infected with *chlorovirus* involves the step of crushing the cells to obtain N-acetyl-D-glucosamine, and therefore has the problem of complex operations, while the method of producing N-acetyl-D-glucosamine using a genetically modified microorganism requires measures for preventing dispersion of the microorganism in facilities, and therefore has the problems of complex operations and antisocial problems related to safety of foods.

Therefore, an object of the preset invention is to provide: a novel microorganism having an ability to produce N-acetyl-D-glucosamine outside the fungal cells and a stable, inexpensive, and safe method of producing N-acetyl-D-glucosamine using a microorganism having an ability to produce N-acetyl-D-glucosamine.

The inventors of the present invention have made extensive studies to achieve the above-mentioned objects. As a result, the inventors first discovered that a certain species of a fungus isolated form nature or a mutant thereof can produce N-acetyl-D-glucosamine in a medium supplemented with a carbon source other than a polymer of N-acetyl-D-glucosamine (chitin) and an oligomer thereof (chitin oligosaccharide). Moreover, they have succeeded in producing N-acetyl-D-glucosamine in a liquid medium at a high concentration by culturing the fungus in the medium and efficiently separating it, thus accomplishing the present invention.

That is, the summary of the present invention is as follows:

(1) A method for producing N-acetyl-D-glucosamine by fermentation comprising:
culturing a non-genetically-recombinant strain of a fungus having an ability to produce N-acetyl-D-glucosamine in a medium supplemented with a carbon source other than chitin and chitin oligosaccharide and a nitrogen source to produce and accumulate N-acetyl-D-glucosamine in the medium; and collecting N-acetyl-D-glucosamine from the medium.

(2) The method for producing N-acetyl-D-glucosamine by fermentation according to (1), wherein the culturing is performed while adding the carbon source and nitrogen source.

(3) The method for producing N-acetyl-D-glucosamine by fermentation according to (1) or (2), wherein the non-genetically-recombinant strain of the fungus having an ability to produce N-acetyl-D-glucosamine is a non-genetically-recombinant strain of a fungus belonging to a genus *Trichoderma*.

(4) The method for producing N-acetyl-D-glucosamine by fermentation according to (3), wherein the non-genetically-recombinant strain of the fungus having an ability to produce N-acetyl-D-glucosamine is a non-genetically-recombinant strain selected from *Trichoderma hamatum, Trichoderma harzianum, Trichoderma reesei*, and *Trichoderma viride*.

(5) The method for producing N-acetyl-D-glucosamine by fermentation according to (4), wherein the non-genetically-recombinant strain of the fungus having an ability to produce N-acetyl-D-glucosamine is *Trichoderma hamatum* AB10282 strain (FERM BP-10623 strain) or *Trichoderma harzianum* AB10283 strain (FERM BP-10624 strain).

(6) A strain having an ability to produce N-acetyl-D-glucosamine selected from *Trichoderma hamatum* FERM BP-10623 strain and *Trichoderma harzianum* FERM BP-10624 strain.

(7) A mutant having an ability to produce N-acetyl-D-glucosamine, which is obtained by introducing a mutation into *Trichoderma hamatum* FERM BP-10623 strain or *Trichoderma harzianum* FERM BP-10624 strain.

DESCRIPTION OF THE PREFERRED EMBODIMENTS

Hereinafter, the present invention will be described in detail.

The method of producing N-acetyl-D-glucosamine of the present invention comprises: culturing a non-genetically-recombinant strain of a fungus having an ability to produce N-acetyl-D-glucosamine in a medium supplemented with a carbon source other than chitin and chitin oligosaccharide and a nitrogen source to produce and accumulate N-acetyl-D-glucosamine in the medium; and separating/purifying N-acetyl-D-glucosamine from the medium to obtain N-acetyl-D-glucosamine.

The non-genetically-recombinant strain of a fungus having an ability to produce N-acetyl-D-glucosamine to be used in the method of the present invention is not particularly limited as long as it is a non-genetically-recombinant fungus having an ability to produce N-acetyl-D-glucosamine, and examples thereof include a fungus isolated from nature based on its ability to produce N-acetyl-D-glucosamine or a mutant thereof. The term "ability to produce N-acetyl-D-glucosamine" as used herein refers to an ability to accumulate N-acetyl-D-glucosamine in a sufficient amount, preferably in an amount of 0.01 mg/mL or more (in the case of shaking culture), more preferably in an amount of 0.1 mg/mL or more (in the case of static culture after shaking culture) when a fungus is cultured in a medium supplemented with a carbon source other than chitin and chitin oligosaccharide and a nitrogen source. Examples of such a fungus include a fungus belonging to the genus *Trichoderma* having an ability to produce N-acetyl-D-glucosamine.

The fungus having an ability to produce N-acetyl-D-glucosamine can be screened by: culturing the fungus in an appropriate medium, preferably in a liquid medium; and determining the presence or absence of N-acetyl-D-glucosamine accumulated in the medium. Detection of N-acetyl-D-glucosamine in a medium can be performed by, for example, an analysis using high-performance liquid chromatography (HPLC) based on comparison with a standard preparation of N-acetyl-D-glucosamine.

Specific examples of the fungus to be used in the present invention include: standard strains such as *Trichoderma hamatum* NBRC31291, *Trichoderma harzianum* NBRC31292, *Trichoderma reesei* ATCC24449, and *Trichoderma viride* NBRC31137; and AB10282 and AB10283 strains which were newly separated from soil samples from Atsugi-shi, Kanagawa by the inventors of the present invention. The newly-separated AB10282 and AB10283 strains belong to the genus *Trichoderma* in the class Hyphomycetes and are examples of fungi having an ability to produce N-acetyl-D-glucosamine and are preferably used in the method of the present invention.

The mycological characteristics of the AB10282 and AB10283 strains are described below.

1. Mycological Characteristics of AB10282 Strain
(1) Cultural/Morphologic Characteristics (a) When AB10282 strain is cultured on corn meal agar medium at 25° C., the diameters of colonies reach 56 to 58 mm at day 2. At day 7 of culture, colonies are flat and have few aerial mycelia. The surfaces and rear surfaces of the colonies are colorless.

(b) When AB10282 strain is cultured on malt extract agar medium at 25° C., the diameters of colonies reach 68 to 70 mm at day 2. At the beginning, the colonies have few aerial mycelia and are white, but aerial mycelia in the form of wool gradually appear. At day 7 of culture, colonies are in the form of wool, and the surfaces of the colonies are pale white. The rear surfaces of the colonies are pale white.

(c) When AB10282 strain is cultured on potato dextrose agar medium at 25° C., the diameters of colonies reach 68 to 70 mm at day 2. The colonies are in the form of cotton wool or in the form of wool, and the surfaces of the colonies are pale white or pale yellowish-white, while the rear surfaces of the colonies are pale white or pale yellowish-white.

(d) When AB10282 strain is cultured on Czapek's agar medium at 25° C., the diameters of colonies reach 29 to 31 mm at day 2. At the beginning, the colonies have few aerial mycelia and are white, but the colonies in the form of cotton wool or wool gradually appear. The surfaces of the colonies are pale white, and the rear surfaces of the colonies are pale white.

(e) AB10282 strain is cultured on corn meal agar medium at 25° for 7 days and observed under an optical microscope, and the results are described below.

The mycelia have septums and extend into the medium and on the medium. The mycelia have widths of 2.0 to 6.0 μm, are colorless and smooth and have septums. The conidiophores are smooth and have septums, and their ends are sometimes sterile and include short and rounded phialides thickly. The phialides extend at approximately right angles to the conidiophores and have short and rounded forms like bowling pins. In addition, the phialides are colorless and smooth and have lengths of 4.0 to 6.0 μm and the maximum width of 2.5 to 3.5 μm. Many conidia are formed from the ends of the phialides, and the conidia are single cells, colorless, smooth, and in the forms of ellipsoid or prolate ellipsoid and have sizes of 3.0 to 4.5×2.4 to 2.8 μm.

(2) Physiological Properties
(a) Growth Temperature

When AB10282 strain is cultured on malt extract agar medium at various temperatures of 5° C., 10° C., 15° C., 20° C., 25° C., 30° C., 35° C., 37° C., and 40° C., the strain grows at any temperature within the range of 10° C. to 30° C., and the optimal growth temperature is about 20 to 25° C.

(b) Growth pH

When AB10282 strain is cultured at 25° C. on malt extract agar media adjusted to pH 3, 4, 5, 6, 7, 8, 9, and 10, the strain grows at pH 3 to 10, and the optimal growth pH is 5 to 6.

2. Mycological Characteristics of AB10283 Strain
(1) Cultural/Morphologic Characteristics
(a) When AB10283 strain is cultured on corn meal agar medium at 25° C., the diameters of colonies reach 63 to 65 mm at day 2. Colonies are flat and then become cotton wool-like or wool-like form. The surfaces of the colonies are grayish green or dark green, and the rear surfaces of the colonies are pale grayish green or pale dark green.

(b) When AB10283 strain is cultured on malt extract agar medium at 25° C., the diameters of colonies reach 76 to 78 mm at day 2. At the beginning, the colonies have few aerial mycelia and are white, but aerial mycelia in the form of cotton wool or wool gradually appear. At day 7 of culture, colonies are in the form of cotton wool or wool, and the surfaces of the colonies become yellowish green or dark green with the formation of conidia. The formation of conidia is observed throughout the colonies except the central region, and the formed conidia are in the forms of rings at the peripheral and middle regions. The rear surfaces of the colonies are yellowish green or dark green.

(c) When AB10283 strain is cultured on potato dextrose agar medium at 25° C., the diameters of colonies reach 63 to 65 mm at day 2. At day 7 of culture, colonies are in the form of cotton wool or wool and have many aerial mycelia and slightly raised central regions, and the central regions of the colonies become yellowish green or pale green with the formation of conidia. The surfaces of the colonies have yellowish green or pale green central regions, and the rear surfaces of the colonies are pale white or pale yellowish white.

(d) When AB10283 strain is cultured on Czapek's agar medium at 25° C., the diameters of colonies reach 35 to 37 mm at day 2. The central regions of the colonies are flat, and the peripheral regions are in the form of cotton wool. The formed conidia are in the forms of rings at the peripheral regions, and the surfaces of the colonies become grayish green or dark green with the formation of conidia. The surfaces of the colonies are grayish green or dark green, and the rear surfaces of the colonies are pale grayish green or pale green.

(e) AB10283 strain is cultured on corn meal agar medium at 25° for 7 days and observed under an optical microscope, and the results are described below.

The mycelia have septums and extend into the medium and on the medium. The mycelia have widths of 2.0 to 8.0 µm, and are colorless and smooth, and have septums. The surfaces of the colonies are colorless and become grayish green or dark green with the formation of conidia. The formation of conidia is observed throughout the colonies, and the formed conidia are in the forms of rings. The conidiophores are smooth and have septums, and phialides extend unthickly at approximately right angles to the conidiophores. The phialides have short and rounded forms like bowling pins, are colorless and smooth, and have lengths of 5.0 to 8.0 µm and the maximum width of 2.5 to 3.5 µm. Many conidia are formed from the ends of the phialides, and they are single cells, colorless, smooth, and in the sphere or sphere-like forms. The sizes are 2.4 to 3.0×2.4 to 2.8 µm, and the ratios of the lengths to the widths are 1.00 to 1.15.

(2) Physiological Properties
(a) Growth Temperature
When AB10282 strain is cultured on malt extract agar medium at various temperatures of 5° C., 10° C., 15° C., 20° C., 25° C., 30 C, 35° C., 37° C., and 40° C., the strain grows at any temperature within the range of 10° C. to 35° C., and the optimal growth temperature is about 25 to 30° C.

(b) Growth pH
When AB10282 strain is cultured at 25° C. on malt extract agar media adjusted to pH 3, 4, 5, 6, 7, 8, 9, and 10, the strain grows at pH 3 to 10, and the optimal growth pH may be 5 to 6.

The taxonomic affiliations of AB10282 and AB10283 strains were searched based on the above-mentioned mycological characteristics by referring to J. A. von Arx, The Genera of Fungi Sporulating in Pure Culture, 3rd ed., J. Cramer, Vaduz, 1981. As a result, AB10282 and AB10283 strains were found to belong to the genus *Trichoderma*. Moreover, the species were identified according to Bokin Bobai written by Toru Okuda, Vol. 20, p. 157-166, 1992, and as a result, AB10282 and AB10283 strains were found to belong to *Trichoderma hamatum* and *Trichoderma harzianum*, respectively. The inventors of the present invention named AB10282 and AB10283 strains "*Trichoderma hamatum* AB10282" and "*Trichoderma harzianum* AB10283", respectively.

AB10282 strain was deposited on May 20, 2005 at International Patent Organism Depositary, National Institute of Advanced Industrial Science and Technology (Chuo Dai-6, 1-1 Higashi 1-chome, Tsukuba-shi, Ibaraki-ken, 305-8566 Japan) under accession number of FERM P-20543, and then the AB10282 strain was transferred to an international deposit based on the provisions of the Budapest treaty and deposited under accession number of FERM BP-10623.

AB10283 strain was deposited on May 20, 2005 at International Patent Organism Depositary, National Institute of Advanced Industrial Science and Technology under accession number of FERM P-20544, and then the AB10283 strain was transferred to an international deposit based on the provisions of the Budapest treaty and deposited under accession number of FERM BP-10624.

*Trichoderma hamatum*, *Trichoderma harzianum*, *Trichoderma reesei*, *Trichoderma viride*, *Trichoderma hamatum* AB10282, and *Trichoderma harzianum* AB10283 strains to be used in the present invention can be preserved on a slant of potato dextrose agar medium. However, natural mutation may occur by subculturing these strains on a slant, and therefore freeze-drying preservation may be performed to preserve these strains stably.

N-acetyl-D-glucosamine-producing fungi such as *Trichoderma hamatum*, *Trichoderma harzianum*, *Trichoderma reesei*, *Trichoderma viride*, AB10282, and AB10283 strains are described above, but the mycological characteristics of general fungi are extremely variable and unstable. It is well known to induce mutations in fungi by natural mutation means or by normal artificial mutation means using ultraviolet irradiation, X-ray irradiation, or a mutagen (such as N-methyl-N-nitro-N-nitrosoguanidine). All strains classified into fungi and having an ability to produce N-acetyl-D-glucosamine, including natural mutants and artificial mutants, can be used in the present invention.

In the case of artificial introduction of a mutation, it is preferable to select a mutant having an ability to produce N-acetyl-D-glucosamine higher than, preferably 1.5-fold or higher than that of a parent strain before introduction of the mutation.

Examples of other fungi belonging to the genus *Trichoderma* include *Trichoderma aureoviride*, *Trichoderma koningi*, and *Trichoderma piluliferm*, and all of them can be used in production of N-acetyl-D-glucosamine.

In order to perform the method of the present invention, a microorganism classified into fungi and having an ability to produce N-acetyl-D-glucosamine is preferably cultured in a medium suitable for a fungus to be used, for example, in a medium supplemented with a nutrient that can be assimilated by a general microorganism, preferably in a liquid medium. Culture of the producing-strain is performed by a general culture method to be used for culture of a microorganism. The medium may be a natural medium or a synthetic medium as long as the medium contains appropriate amounts of a carbon source, a nitrogen source, and an inorganic salt and the like, which can be assimilated by the fungus.

The method of producing N-acetyl-D-glucosamine by fermentation of the present invention is performed not by a degradation reaction in which N-acetyl-D-glucosamine is produced by degrading a polymer of N-acetyl-D-glucosamine (chitin) and an oligomer thereof (chitin oligosaccharide) contained in a medium as raw materials, but by a biosynthesis reaction of chitin, which is a component of cell walls of a fungus, to produce N-acetyl-D-glucosamine as an intermediate of the reaction. Therefore, a carbon source other than chitin and chitin oligosaccharide and a nitrogen source are used as a carbon and a nitrogen source.

Examples of the carbon source to be used as a raw material include glucose, fructose, sucrose, galactose, dextrin, glycerol, starch, starch syrup, molasses, and animal/vegetable oil. On the other hand, examples of the nitrogen source include fish flour, soybean flour, wheat germ, corn steep liquor, cottonseed meal, meat extract, peptone, yeast extract, ammonium chloride, ammonium sulfate, ammonium nitrate, ammonium acetate, sodium nitrate, and urea. In addition, if necessary, the medium may contain an inorganic salt that can provide sodium, potassium, calcium, magnesium, cobalt, manganese, chlorine, phosphate, sulfate, or other ion. Moreover, the medium may contain an inorganic substance and (or) an organic substance capable of enhancing growth of the N-acetyl-D-glucosamine-producing fungus to be used and promoting production of N-acetyl-D-glucosamine.

It is preferable to add the carbon source and nitrogen source not only at the beginning of culture but also during culture. Specifically, the carbon source and nitrogen source are desirably added before they are completely consumed while monitoring the concentrations of the carbon source and nitrogen source in a medium.

Examples of a medium suitable for growth of fungi belonging to the genus Trichoderma, Trichoderma hamatum AB10282, and Trichoderma harzianum AB10283 strains include potato dextrose agar medium, malt extract agar medium, and V-8 juice agar medium. Examples of a medium suitable for production of N-acetyl-D-glucosamine include Czapek's (modified) medium besides the media shown in Examples.

Preferable examples of a method of culturing a fungus having an ability to produce N-acetyl-D-glucosamine include a culture method under aerobic conditions and submerged liquid culture under aeration. The culture temperature is preferably 15 to 30° C., more preferably 25 to 30° C. The level of accumulated N-acetyl-D-glucosamine varies depending on the type of a medium used and culture conditions, but in general, the level of accumulation reaches the maximum level after 3- to 20-day culture of shaking culture, static culture, or tank culture.

The culture conditions for efficiently producing N-acetyl-D-glucosamine may be set by appropriately adjusting or selecting the composition of the medium components, culture temperature, stirring speed, pH, aeration amount, preculture time, amount of an inoculum, etc. depending on the species of a fungus to be used, external conditions, etc. If foams are formed during liquid culture, an antifoamer such as silicone oil, a vegetable oil, or a surfactant may be appropriately added to a medium singly or in combination thereof.

For terminating culture, culture is preferably stopped at the time when the level of N-acetyl-D-glucosamine accumulated in a culture reaches the maximum level. N-acetyl-D-glucosamine is preferably isolated from the culture in accordance with a general method of obtaining a fermentation product. Specifically, N-acetyl-D-glucosamine may be isolated from a medium by, for example, ion-exchange chromatography, activated carbon treatment, crystallization, membrane separation, or the like.

The present invention will be described in more detail by referring to Examples. However, the present invention is not limited to the following embodiments.

EXAMPLE 1

100 ml of a pH-unadjusted medium supplemented with 4.0% glucose, 0.1% ammonium sulfate, 0.4% yeast extract, 0.01% magnesium sulfate, 0.02% potassium dihydrogen phosphate, and 0.18% dipotassium hydrogen phosphate was added to a 500-ml baffled conical flask, and one platinum loop of fungus belonging to the genus *Trichoderma* was inoculated from a slant into the medium, followed by aerobic culture at 180 rpm with a rotary shaker at 27° C. for 5 days, and then static culture at 27° C. for 2 days. The culture supernatants were analyzed by HPLC, and the results were compared with those of a standard preparation of N-acetyl-D-glucosamine. As a result, the products in all the strains were identified as N-acetyl-D-glucosamine.

HPLC Conditions
Column; Wakosil 5NH2 column (($\Phi$4.6 mm×250 mm),
Mobile phase; acetonitrile:water=80:20,
Flow rate; 2 ml/min,
Column temperature; 20° C.,
Detection; RI The production levels of N-acetyl-D-glucosamine by the respective cultured fungi belonging to the genus *Trichoderma* are shown in Table 1.

TABLE 1

| N-acetyl-D-glucosamine level in culture supernatant | |
|---|---|
| Strains | N-acetyl-D-glucosamine (mg/ml) |
| *Trichoderma hamatum* NBRC31291 | 0.8 |
| *Trichoderma harzianum* NBRC31292 | 0.7 |
| *Trichoderma reesei* ATCC24449 | 0.5 |
| *Trichoderma viride* NBRC31137 | 0.5 |
| AB10282 | 1.0 |
| AB10283 | 0.8 |

EXAMPLE 2

Introduction of Mutation by Ultraviolet Irradiation

The conidia of *Trichoderma hamatum* AB10282 were suspended in 10 ml of phosphate buffer (pH 6.0). The conidium solution was transferred to a dish, and a stirring bar was placed therein and rotated with a stirrer while performing irradiation using a 20 W-ultraviolet lamp from a distance of 20 cm for three minutes. After ultraviolet irradiation, the conidium solution was diluted and spread on a plate agar supplemented with 4.0% corn starch, 0.1% ammonium chloride, 0.4% yeast extract, 0.1% magnesium sulfate, 0.02% potassium dihydrogen phosphate, 0.08% disodium hydrogen phosphate 12-hydrate, and 1.5% agar (pH 7.0), and the resultant colonies were separated. The separated colonies were inoculated into test tubes, each containing 5 ml of a medium supplemented with 4.0% corn starch, 0.1% ammonium chloride, 0.4% yeast extract, 0.1% magnesium sulfate, 0.02% potassium dihydrogen phosphate, and 0.08% disodium hydrogen phosphate 12-hydrate (pH 7.0), and cultured with shaking at 27° C. for seven days, to select a mutant which produces N-acetyl-D-glucosamine in a larger amount than that of the AB10282 strain.

Production of N-acetyl-D-glucosamine 200 ml of a medium supplemented with 4.0% corn starch, 0.1% ammonium chloride, 0.4% yeast extract, 0.1% magnesium sulfate, 0.02% potassium dihydrogen phosphate, and 0.08% disodium hydrogen phosphate 12-hydrate (pH 7.0) was added to a 500-ml baffled conical flask, and one platinum loop of the mutant of *Trichoderma hamatum*, which had been modified by ultraviolet irradiation so as to produce N-acetyl-D-glucosamine in a larger amount, was inoculated from a slant into the medium and aerobically cultured at 180 rpm with a rotary shaker at 27° C. Then, the mutant was cultured for 15 days with addition of 2 ml of 50% glucose/5% ammonium acetate solution at days 6, 7, 8, 10, and 12. The culture supernatants were analyzed by HPLC, and the results were compared with those of a standard preparation of N-acetyl-D-glucosamine. As a result, the product was identified as N-acetyl-D-glucosamine. This culture yielded a medium containing 5 mg/ml N-acetyl-D-glucosamine.

EXAMPLE 3

Introduction of Mutation by Mutagen

The conidia of *Trichoderma harzianum* AB10283 were suspended in 4 ml of citrate buffer (pH 6.0). N-methyl-N-nitro-N-nitrosoguanidine was added to the conidium solution (final concentration 50 µl/ml), followed by incubation at 37° C. for 30 minutes. Thereafter, centrifugation (3,500 x g) was performed, and the supernatant was removed. Then, the conidia were suspended in the citrate buffer (pH 6.0) again, and washed by centrifugation. The conidium solution treated with N-methyl-N-nitro-N-nitrosoguanidine was diluted and spread on a plate agar supplemented with 4.0% corn starch, 0.1% ammonium chloride, 0.4% yeast extract, 0.1% magnesium sulfate, 0.02% potassium dihydrogen phosphate, 0.08% disodium hydrogen phosphate 12-hydrate, and 1.5% agar (pH 7.0), and the resultant colonies were separated. The separated colonies were inoculated into test tubes, each containing 5 ml of a medium supplemented with 4.0% corn starch, 0.1% ammonium chloride, 0.4% yeast extract, 0.1% magnesium sulfate, 0.02% potassium dihydrogen phosphate, and 0.08% disodium hydrogen phosphate 12-hydrate (pH 7.0) and cultured with shaking at 27° C. for seven days, to select a mutant which produces N-acetyl-D-glucosamine in a larger amount than that of the AB10283 strain.

Production of N-acetyl-D-glucosamine 200 ml of a medium supplemented with 4.0% corn starch, 0.1% ammonium chloride, 0.4% yeast extract, 0.02% potassium dihydrogen phosphate, and 0.08% disodium hydrogen phosphate 12-hydrate (pH 7.0) was added to a 500-ml baffled conical flask, and one platinum loop of the mutant of *Trichoderma harzianum*, which had been mutated by N-methyl-N-nitro-N-nitrosoguanidine so as to produce N-acetyl-D-glucosamine in a larger amount, was inoculated from a slant into the medium and aerobically cultured at 180 rpm with a rotary shaker at 27° C. Then, the mutant was cultured for 15 days with addition of 2 ml of 50% glucose/5% ammonium acetate solution at days 6, 7, 8, 10, and 12. The culture supernatants were analyzed by HPLC, and the results were compared with those of a standard preparation of N-acetyl-D-glucosamine. As a result, the product was identified as N-acetyl-D-glucosamine. This culture yielded a medium containing 3 mg/ml N-acetyl-D-glucosamine.

EXAMPLE 4

75 ml of a medium supplemented with 6.0% glucose, 0.1% ammonium chloride, 0.6% yeast extract, 0.02% potassium dihydrogen phosphate, and 0.08% disodium hydrogen phosphate 12-hydrate (pH 7.0) was added to a 500-ml baffled conical flask, and one platinum loop of the mutant of *Trichoderma hamatum*, which had been mutated in Example 2 with ultraviolet irradiation so as to produce N-acetyl-D-glucosamine in a larger amount, was inoculated from a slant into the medium and aerobically cultured at 180 rpm with a rotary shaker at 27° C. Then, the mutant was cultured for 15 days after 2 ml of 50% glucose/5% ammonium acetate solution had been added thereto at days 4, 7, 9, 11, and 13. The culture supernatants were analyzed by HPLC, and the results were compared with those of a standard preparation of N-acetyl-D-glucosamine. As a result, the product was identified as N-acetyl-D-glucosamine. This culture yielded a medium containing 13 mg/ml N-acetyl-D-glucosamine.

EXAMPLE 5

2.0 L of a medium supplemented with 6.0% glucose, 0.1% ammonium chloride, 0.6% yeast extract, 0.02% potassium dihydrogen phosphate, 0.08% disodium hydrogen phosphate 12-hydrate (pH 7.0) was added to a 4 L-jar fermenter and sterilized, and the precultured *Trichoderma hamatum* mutant, which had been mutated in Example 2 with ultraviolet irradiation so as to produce N-acetyl-D-glucosamine in a larger amount, was inoculated therein. Then, the strain was cultured at 27° C. for 10 days at a stirring rate of 450 rpm and an aeration rate of 2 L/min with addition of 20 ml of 50% glucose/5% ammonium acetate solution at days 3, 5, 7, and 9.

N-acetyl-D-glucosamine in the supernatant was measured by HPLC, and the concentration of N-acetyl-D-glucosamine was found to be 15 mg/ml. The supernatant obtained by centrifugation of 2.0 L of the medium was passed through a column filled with 200 mL of activated carbon, and 200 ml of ion-exchanged water was passed through the column. Then, the flow-through solution was passed through a column filled with 200 ml of a strong-acid cation exchange resin, DUOLITE (registered trademark) C-20 ($H^+$-type), and 200 ml of ion-exchanged water was passed through the column. The obtained flow-through solution was further passed through a column filled with 200 ml of a weakly-basic anion exchange resin, DUOLITE (registered trademark) A378D ($OH^-$-type), and 200 ml of ion-exchanged water was passed through the column.

The obtained flow-through solution was concentrated and dried under reduced pressure, to thereby yield 20 g of a solid product. Crystallization was performed by adding 50 ml of acetone to an aqueous solution obtained by dissolving the product in 20 ml of distilled water, to thereby yield 12 g of N-acetyl-D-glucosamine crystalline powder with a purity of 95% as crystalline powder. An NMR analysis of the resultant crystalline powder revealed that the $^1$H-NMR chemical shift value and $^{13}$C-NMR chemical shift value corresponded to literature values of N-acetyl-D-glucosamine.

INDUSTRIAL APPLICABILITY

The method of producing N-acetyl-D-glucosamine of the present invention can realize stable production/supply of N-acetyl-D-glucosamine, and this method can achieve efficient, safe, and inexpensive production of N-acetyl-D-glucosamine. In addition, the microorganisms of the present invention can be preferably used in the method of producing N-acetyl-D-glucosamine as described above.

What is claimed is:

1. A strain having an ability to produce N-acetyl-D-glucosamine selected from *Trichoderma hamatum* FERM BP-10623 strain and *Trichoderma harzianum* FERM BP-10624 strain.

* * * * *

UNITED STATES PATENT AND TRADEMARK OFFICE
CERTIFICATE OF CORRECTION

PATENT NO. : 7,998,723 B2
APPLICATION NO. : 11/995104
DATED : August 16, 2011
INVENTOR(S) : Mori et al.

It is certified that error appears in the above-identified patent and that said Letters Patent is hereby corrected as shown below:

Column 1, Line 52, "by a microorganism_(for" should be changed to --by a microorganism (for--

Column 4, Line 42, "at 25° for 7" should be changed to --at 25° C. for 7--

Column 5, Line 43, "at 25° for 7" should be changed to --at 25° C. for 7--

Column 5, Line 65, "25° C., 30 C, 35° C.," should be changed to --25° C., 30° C., 35° C.,--

Column 6, Lines 61-62, "*Trichoderma koningi*, and *Trichoderma piluliferm*," should be changed to
--*Trichoderma koningii*, and *Trichoderma piluliferum*,--

Column 8, Line 30, "column ((Φ4.6 mm × 250 mm)," should be changed to
--column (Φ4.6 mm × 250 mm),--

Signed and Sealed this
Eighth Day of May, 2012

David J. Kappos
*Director of the United States Patent and Trademark Office*